US010746654B2

(12) United States Patent
Klapproth et al.

(10) Patent No.: US 10,746,654 B2
(45) Date of Patent: Aug. 18, 2020

(54) METHOD FOR MONITORING THE CORRESPONDENCE OF A BEER SAMPLE WITH A REFERENCE BEER

(71) Applicant: QFood GmbH, Gundelfingen (DE)

(72) Inventors: Holger Klapproth, Freiburg im Breisgau (DE); Robert Seidel, Freiburg im Breisgau (DE); Joachim Haas, Freiburg im Breisgau (DE); Jonathan E. Green, Gundelfingen (DE)

(73) Assignee: QFood GmbH, Gundelfingen (DE)

( * ) Notice: Subject to any disclaimer, the term of this patent is extended or adjusted under 35 U.S.C. 154(b) by 0 days.

(21) Appl. No.: 16/324,292

(22) PCT Filed: Aug. 3, 2017

(86) PCT No.: PCT/EP2017/069698
§ 371 (c)(1),
(2) Date: Feb. 8, 2019

(87) PCT Pub. No.: WO2018/029088
PCT Pub. Date: Feb. 15, 2018

(65) Prior Publication Data
US 2019/0178794 A1 Jun. 13, 2019

(30) Foreign Application Priority Data

Aug. 10, 2016 (DE) .................. 10 2016 009 636

(51) Int. Cl.
*G01N 21/3577* (2014.01)
*G01N 33/14* (2006.01)
*G06F 17/18* (2006.01)
*G01N 21/84* (2006.01)

(52) U.S. Cl.
CPC ....... *G01N 21/3577* (2013.01); *G01N 33/146* (2013.01); *G06F 17/18* (2013.01); *G01N 33/143* (2013.01); *G01N 2021/8411* (2013.01); *G01N 2021/8416* (2013.01); *G01N 2201/129* (2013.01)

(58) Field of Classification Search
None
See application file for complete search history.

(56) References Cited

U.S. PATENT DOCUMENTS

| 5,446,681 A | 8/1995 | Gethner et al. | |
| 2007/0254063 A1* | 11/2007 | Aerts | C23C 3/12 |
| | | | 426/11 |
| 2010/0303994 A1* | 12/2010 | Aerts | C12H 1/22 |
| | | | 426/592 |
| 2011/0135784 A1* | 6/2011 | Tanner | A23L 7/20 |
| | | | 426/2 |
| 2011/0151068 A1* | 6/2011 | Taylor | A23F 3/163 |
| | | | 426/115 |
| 2015/0060674 A1 | 3/2015 | Levels et al. | |
| 2016/0194586 A1* | 7/2016 | Nordkvist | G01N 21/552 |
| | | | 426/16 |
| 2016/0369214 A1* | 12/2016 | Mosher | G01N 21/3577 |

FOREIGN PATENT DOCUMENTS

| DE | 69128357 T2 | 7/1998 |
| DE | 10108712 A1 | 9/2002 |
| WO | 2012167805 A1 | 12/2012 |

OTHER PUBLICATIONS

Foyolle et al., "Determination of Major Compounds of Alcoholic Fermentation by Middle-Infrared Spectroscopy: Study of Temperature Effects and Calibration Methods", Applied Spectroscopy, The Society for Applied Spectroscopy, 1996, pp. 1325-1330, vol. 50, No. 10, Baltimore.

* cited by examiner

*Primary Examiner* — Hoon K Song
(74) *Attorney, Agent, or Firm* — The Webb Law Firm

(57) ABSTRACT

In a method for monitoring the correspondence of a beer sample with a reference beer, at least 15 reference beer samples of the reference beer are brewed with the same ingredients and the same process parameters. Measurement signals for the absorption spectrum of the reference beer samples are captured and a principal component analysis is carried out for the measurement signals, in which at least 15 principal components are ascertained. A factor loading $P_R(i, j)$ is respectively determined for each principal component for the individual reference beer samples and a reference value (I) is ascertained, where i denotes the reference beer sample and j denotes the principal component, $\mu_R(j)$ refers to the mean value of all factor loadings of the j-th principal component and $\sigma_P(j)$ refers to the standard deviation of these factor loadings. A reference interval (II) is formed, where n denotes the number of reference beer samples, m denotes the number of principal components, $\sigma_R(j)$ denotes the standard deviation of all reference values of the j-th principal component and k denotes a constant not equal to zero. A measurement signal is captured for the absorption spectrum of the beer sample and the factor loadings $P_B(i)$ of this measurement signal are determined for the principal components ascertained for the reference beer samples and a characteristic (III) is formed and compared to the reference interval. Should the characteristic B lie outside of the reference interval, a fault during the production of the beer sample is indicated.

5 Claims, No Drawings

METHOD FOR MONITORING THE CORRESPONDENCE OF A BEER SAMPLE WITH A REFERENCE BEER

CROSS-REFERENCE TO RELATED APPLICATIONS

This application is the United States national phase of International Application No. PCT/EP2017/069698 filed Aug. 3, 2017, and claims priority to German Patent Application No. 10 2016 009 636.5 filed Aug. 10, 2016, the disclosure of each of which is hereby incorporated by reference in its entirety.

BACKGROUND OF THE INVENTION

Field of the Invention

The invention relates to a method for monitoring the correspondence of a beer sample with a reference beer, which is assigned to the same beer variety as the beer sample.

Description of Related Art

In breweries, demanding quality controls are performed during beer production, which in addition to testing the beers produced for bacteria, also include sensory evaluation of the beers. The purpose of the sensory evaluation is to ensure that beers of a specific beer variety produced in the brewery always have the same flavor and aroma typical of that brewery. These measures serve to distinguish the beers of the brewery in question and set them apart from competitor products. It is expected that beer consumers will become accustomed to the flavor and induced to obtain their beer from the brewery in question.

In practice, sensory evaluation of beers takes place in the context of beer tastings, which in larger breweries are performed by a trained tasting team. However, the problem with beer tasting is that the taste perception of the beer tasters can change when tasting several beers in succession. This is because the sense of taste of the beer taster is still neutral when tasting the first beer sample, but may be altered by the first beer sample when tasting the next beer sample. This can lead to inaccuracies during the quality evaluation. Also disadvantageous is the fact that the sensory evaluation of beers by tasting is rather demanding and that the tasting team may not always be available.

The object is therefore that of developing a method of the aforementioned type, which makes it possible to monitor the correspondence of a beer sample produced in a brewery with a reference beer of the same beer variety in an expedient and reproducible manner in the brewery.

Summary of the Invention

According to the invention, a method is provided such that at least 15 reference beer samples of the reference beer are brewed with the same ingredients and the same process parameters, measurement signals for the absorption spectrum of the individual reference beer samples are captured by means of infrared absorption spectroscopy and a principal component analysis is performed for the measurement signals, in which at least 15 principal components are ascertained and a factor loading $P_R(i,j)$ is respectively determined for each principal component for the individual reference beer samples, wherein i denotes the reference beer sample and j denotes the principal component, that a reference value $$R(i,j) = \left| \frac{P_R(i,j) - \mu_P(j)}{\sigma_P(j)} \right|$$

is respectively calculated from the factor loadings $P_R(i,j)$ for each reference beer sample and for each principal component, wherein $\mu_P(j)$ refers to the mean of all factor loadings of the $j^{th}$ principal component and $\sigma_P(j)$ refers to the standard deviation of these factor loadings, that a reference interval $$\left[ \frac{k}{n} \sum_{i=1}^{n} \sum_{j=1}^{m} R(i,j) - k \sum_{j=1}^{m} \sigma_R(j) - \frac{k}{n} \sum_{i=1}^{n} \sum_{j=1}^{m} R(i,j) + k \sum_{j=1}^{m} \sigma_R(j) \right]$$

is formed, wherein n is the number of reference beer samples, m is the number of principal components, $\sigma_P(j)$ is the standard deviation of all reference values of the $j^{th}$ principal component and k is a constant not equal to zero, that a measurement signal for the absorption spectrum of the beer sample to be evaluated for correspondence with the reference beer is captured by means of infrared absorption spectroscopy, and the factor loadings $P_B(i)$ of this measurement signal are determined for the principal components ascertained for the reference beer samples and from these factor loadings $P_B(i)$, from the means $\mu_P(j)$ of the factor loadings of the reference beer samples for the individual principal components, and from the standard deviations $\sigma_P(j)$ of the factor loadings, a characteristic value $$B = k \sum_{j=1}^{m} \left| \frac{P_B(j) - \mu_P(j)}{\sigma_P(j)} \right|$$

is formed and compared to the reference interval, and that an error during the production of the beer sample is indicated should the characteristic value B lie outside of the reference interval.

Advantageously, the reference interval is determined with the aid of normalized reference values $R(i,j)$, in which the mean $\mu_P(j)$ of all factor loadings of the relevant principal components is subtracted from the factor loading $P_R(i,j)$ assigned to the relevant reference beer sample, and the result of this subtraction is divided by the standard deviation of all reference values $R(i,j)$ of this principal component. This measure ensures that spectral components caused by beer ingredients present only in low concentrations in the reference beer samples are factored into the reference interval to a greater extent than would be the case if the factor loadings rather than the normalized reference values were used to calculate the reference interval. A precise comparison of the beer sample to the reference beer represented by the reference beer samples is thus possible.

The factor loadings (aka "scores") can be ascertained by means of a suitable software known per se. The constant k can have any value not equal to zero, in particular the value 1 or the reciprocal value 1/m of the number m of principal components. After the reference interval has been calculated from the factor loadings and the constant, it can be filed together with the principal components and optionally the constant k in a memory of a microcomputer, for example.

With the previously stored principal components, the reference interval, and optionally the factor k, the method according to the invention can be used in an expedient manner on a plurality of beer samples produced in a brewery, wherein a measurement signal for the absorption spectrum is recorded from each relevant beer sample by means of a high-resolution absorption spectrometer. In this process, this absorption spectrum is captured with the same parameters as the absorption spectra of the reference beer samples. The same absorption spectrometer, or at least one of the same design as the absorption spectrometer used to measure the absorption spectra of the reference beer samples, is preferably used to measure the absorption spectrum of the beer sample.

With the aid of an operating program running on the microcomputer, it is possible to calculate the characteristic value B from the measurement signal and from the principal components, compare it to the reference interval, and display the result of the comparison. Should the comparison indicate a deviation, if need be the brew master or other qualified employee of the brewery can verify the quality of the tested beer sample by tasting, and if necessary, modify the production parameters for the beer production in such a way that the error is compensated or eliminated.

The microcomputer can be integrated in the absorption spectrometer or in the control of the same. This enables an expedient onsite monitoring of the beer samples during the production process. However, the microcomputer can also be separate from the absorption spectrometer and connectable to the absorption spectrometer via a suitable interface for scanning in the measurement signal for the absorption spectrum.

In a preferred embodiment of the invention, the number n of reference beer samples is greater than or equal to the number m of principal components, in particular twice as great and preferably at least three times as great as the latter. Inaccuracies in the principal components caused by statistical variations can be avoided to the greatest possible extent by having the largest possible number of reference beer samples.

In a preferred embodiment of the invention, the number m of principal components is at least 20, optionally at least 30, in particular at least 40, and preferably at least 50. This permits a very precise comparison of the beer sample to the reference beer, in which deviations of beer ingredients contained in the beer sample and/or in the reference beer only in very low concentrations can also be taken into account.

During the infrared absorption spectroscopy, it is advantageous if the reference beer samples and the beer sample are irradiated with infrared radiation, the wave number of which covers the range between 950 and 3050, in particular between 960 and 2000, and preferably between 980 and 1200. In this range, the sugars contained in the beer have characteristic value absorption peaks, which can be identified in the spectrum. During the measurement of the absorption spectrum, a fluid layer of the beer sample or of the reference beer sample is irradiated with infrared radiation. The thickness of the fluid layer irradiated with infrared radiation can be at most 30 µm, optionally at most 20 µm, preferably at most 15 µm, and in particular at most 10 µm.

DESCRIPTION OF THE INVENTION

An exemplary embodiment of the invention will be explained in more detail in the following.

In the exemplary embodiment, for monitoring the correspondence of a beer sample to be tested with a reference beer, which is assigned to the same beer variety as the beer sample, 100 reference beer samples of the reference beer are brewed with the same ingredients and the same process parameters in each case.

Using a QFOOD QUANTOS®-type infrared absorption spectrometer, measurement signals are captured for the absorption spectra of the 100 reference beer samples in a wave number range extending from the wave number 980 to the wave number 1200. Each measurement signal respectively comprises 1000 value combinations, each of which has at least one value for the wave number and a value assigned to this wave number for the optical infrared absorption of the reference beer sample.

A principal component analysis is performed for the 100 measurement signals or spectra captured in this manner, in which 30 principal components are ascertained using a software known per se. A factor loading $P_R(i,j)$ is respectively determined for each of the 30 principal components for the 100 reference beer samples. The index i denotes the reference beer sample and the index j denotes the principal component. This gives rise to 3,000 factor loadings $P_R(i,j)$ in total, only a few of which are shown below for the sake of clarity:

|  | j = 1 | j = 2 | j = 3 | ... | j = 29 | j = 30 |
|---|---|---|---|---|---|---|
| i = 1 | −0.1230054 | −0.0026305 | −0.0003498 | ... | −0.00000534 | −0.00000243 |
| i = 2 | −0.1242563 | −0.0026599 | −0.0003300 | ... | 0.00000015 | −0.00000127 |
| i = 3 | −0.1293215 | −0.0019354 | 0.0000951 | ... | −0.00000968 | 0.00000739 |
| i = 98 | −0.1294580 | −0.0003328 | 0.00057318 | ... | −0.00000786 | −0.00000556 |
| i = 99 | −0.1286656 | −0.0008917 | 0.00045053 | ... | −0.00000487 | −0.00000637 |
| i = 100 | −0.1309384 | −0.0004471 | 0.00042969 | ... | −0.00000069 | −0.00000744 |

The mean $\mu_P(j)$ of all factor loadings and the standard deviation $\sigma_P(j)$ of these factor loadings are respectively determined for each of the 30 principal components:

| j | $\mu_P(j)$ | $\sigma_P(j)$ |
|---|---|---|
| 1 | −0.12897300 | 0.00196521 |
| 2 | −0.00115020 | 0.00124260 |
| 3 | 0.00052527 | 0.00039921 |
| 28 | 0.00000017708 | 0.0000102710 |
| 29 | 0.00000015864 | 0.0000089216 |
| 30 | 0.00000016190 | 0.0000060188 |

For each factor loading $P_R(i,j)$, respectively, a positive reference value $R(i,j)$ is calculated:

| i | R(i, 1) | R(i, 2) | R(i, 3) | ... | R(i, 29) | R(i, 30) |
|---|---------|---------|---------|-----|----------|----------|
| 1 | 3.03662653 | 1.19134758 | 2.19197238 | ... | 0.61632769 | 0.43063337 |
| 2 | 2.40007829 | 1.21500130 | 2.14247494 | ... | 0.00063217 | 0.23790443 |
| 3 | 0.17732606 | 0.63194497 | 1.07755101 | ... | 1.10278655 | 1.20091677 |
| 98 | 0.24679333 | 0.65777029 | 0.12001654 | ... | 0.89878767 | 0.95066921 |
| 99 | 0.15641331 | 0.20799952 | 0.18721578 | ... | 0.56364666 | 1.08524718 |
| 100 | 1.00010092 | 0.56582482 | 0.23942857 | ... | 0.09467341 | 1.26302301 | according to the absolute value formula $$R(i, j) = \left| \frac{P_R(i, j) - \mu_P(j)}{\sigma_P(j)} \right|$$

For each main component, respectively, the standard deviation $\sigma_R(i)$ over all 100 reference values of the relevant principal component is furthermore determined:

| i | $\sigma_R(i)$ |
|---|---------------|
| 1 | 0.64967043 |
| 2 | 0.54158537 |
| 3 | 0.57910532 |
| 28 | 0.60052400 |
| 29 | 0.72734766 |
| 30 | 0.63994051 |

From the reference values R(i,j) and standard deviations $\sigma_R(i)$ thus obtained, a reference interval: [21.1333601−12.0965087 ... 21.1333601+12.0965087]=[9.0368514 ... 33.2298688]
is formed according to the formula:

$$\left[ \frac{1}{100 \cdot 30} \sum_{i=1}^{100} \sum_{j=1}^{30} R(i, j) - \frac{1}{30} \sum_{i=1}^{30} \sigma_R(j) - \frac{1}{100 \cdot 30} \sum_{i=1}^{100} \sum_{j=1}^{30} R(i, j) + \frac{1}{30} \sum_{i=1}^{30} \sigma_R(j) \right]$$

The beer sample to be checked for correspondence with the reference beer is provided in a further method step. Using the QFOOD QUANTOS®-type infrared absorption spectrometer, a measurement signal for the absorption spectrum of the beer sample is captured in the same wave number range as the one in which the absorption spectra of the reference beer samples were measured.

The factor loadings $P_B(i)$ of this measurement signal are determined for the 30 principal components ascertained for the reference beer samples:

| i | $\sigma_R(i)$ |
|---|---------------|
| 1 | 0.64967043 |
| 2 | 0.54158537 |
| 3 | 0.57910532 |
| 28 | 0.60052400 |
| 29 | 0.72734766 |
| 30 | 0.63994051 |

The factor loadings thus obtained are normalized by subtracting the mean $\mu_P(j)$ of all factor loadings of the reference beer samples for the relevant principal component from the relevant factor loading $P_B(j)$ and dividing the result, in absolute value, of this subtraction by the standard deviation $\sigma_P(j)$ of these factor loadings:

$$\left| \frac{P_B(j) - \mu_P(j)}{\sigma_P(j)} \right|$$

The arithmetic mean is calculated from the normalized factor loadings thus obtained in order to form a characteristic value B for the beer sample:

$$B = \frac{1}{30} \sum_{j=1}^{m} \left| \frac{P_B(j) - \mu_P(j)}{\sigma_P(j)} \right| = 52.28199576$$

This characteristic value B is compared to the reference interval [9.0368514 ... 33.2298688]. The characteristic value B lies outside of the reference interval, thus indicating an error during the production of the beer sample.

The invention claimed is:
1. A method for monitoring the correspondence of a beer sample with a reference beer that is assigned to the same beer variety as the beer sample, characterized in that at least 15 reference beer samples of the reference beer were brewed with the same ingredients and the same process parameters, that infrared absorption spectroscopy is used to capture measurement signals for the absorption spectrum of the individual reference beer samples and a principal component analysis is performed for the measurement signals, in which at least 15 principal components are ascertained and a factor loading $P_R(i,j)$ is respectively determined for each principal component for the individual reference beer samples, wherein i denotes the reference beer sample and j denotes the principal component, that a reference value

$$R(i, j) = \left| \frac{P_R(i, j) - \mu_P(j)}{\sigma_P(j)} \right|$$

is respectively calculated from the factor loadings $P_R(i,j)$ for each reference beer sample and for each principle component, wherein $\mu_P(j)$ refers to the mean of all factor loadings of the $j^{th}$ principal component and $\sigma_P(j)$ refers to the standard deviation of these factor loadings, that a reference interval $$\left[ \frac{k}{n} \sum_{i=1}^{n} \sum_{j=1}^{m} R(i, j) - k \sum_{j=1}^{m} \sigma_R(j) - \frac{k}{n} \sum_{i=1}^{n} \sum_{j=1}^{m} R(i, j) + k \sum_{j=1}^{m} \sigma_R(j) \right]$$

is formed, wherein n is the number of reference beer samples, m is the number of principal components, $\sigma_R(j)$ is the standard deviation of all reference values of the $j^{th}$ principal component and k is a constant not equal to zero, that infrared absorption spectroscopy is used to capture a measurement signal for the absorption spectrum of the beer sample to be checked for correspondence with the reference beer and the factor loadings $P_B(i)$ of this measurement signal are determined for the principal components ascertained for the reference beer samples and from these factor loadings $P_B(i)$, from the means $\mu_p(j)$ of the factor loadings of the reference beer samples for the individual principal components, and from the standard deviations $\sigma_P(j)$ of these factor loadings, a characteristic value $$B = k\sum_{j=1}^{m}\left|\frac{P_B(j) - \mu_P(j)}{\sigma_P(j)}\right|$$

is formed and compared to the reference interval, and that an error during the production of the beer sample is indicated should the characteristic value B lie outside of the reference interval.

2. The method according to claim 1, characterized in that the number n of reference beer samples is greater than or equal to the number m of principal components, in particular twice as great and preferably at least three times as great as the latter.

3. The method according to claim 1, characterized in that the number m of principal components is at least 20, optionally at least 30, in particular at least 40, and preferably at least 50.

4. The method according to claim 1, characterized in that the constant k corresponds to the reciprocal of the number m of the principal components.

5. The method according to claim 1, characterized in that during the infrared absorption spectroscopy, the reference beer samples and the beer sample are irradiated with infrared radiation, the wave number of which covers the range between 950 and 3050, in particular between 960 and 2000, and preferably between 980 and 1200.

* * * * *